US008030355B2

(12) United States Patent
Jansen et al.

(10) Patent No.: US 8,030,355 B2
(45) Date of Patent: Oct. 4, 2011

(54) TABLET COMPOSITION WITH A PROLONGED RELEASE OF TAMSULOSIN

(75) Inventors: Korinde Annemarie Jansen, Loo (NL); Farid Abedin Dorkoosh, Utrecht (NL)

(73) Assignee: Synthon BV, Nijmegen (NL)

( * ) Notice: Subject to any disclaimer, the term of this patent is extended or adjusted under 35 U.S.C. 154(b) by 1140 days.

(21) Appl. No.: 11/749,849

(22) Filed: May 17, 2007

(65) Prior Publication Data
US 2007/0269514 A1 Nov. 22, 2007

Related U.S. Application Data

(60) Provisional application No. 60/801,135, filed on May 17, 2006, provisional application No. 60/914,148, filed on Apr. 26, 2007.

(51) Int. Cl.
*A61K 31/18* (2006.01)
*A61K 9/20* (2006.01)
*A61K 9/22* (2006.01)

(52) U.S. Cl. ........ 514/603; 514/960; 514/961; 514/964; 424/408; 424/464; 424/468

(58) Field of Classification Search .................. 424/408, 424/464, 468; 514/603, 960, 961, 964
See application file for complete search history.

(56) References Cited

U.S. PATENT DOCUMENTS

| | | | |
|---|---|---|---|
| 4,217,305 A | 8/1980 | Imai et al. | |
| 4,703,063 A | 10/1987 | Imai et al. | |
| 4,731,478 A | 3/1988 | Niigata et al. | |
| 4,772,475 A * | 9/1988 | Fukui et al. | 424/468 |
| 4,868,216 A | 9/1989 | Imai et al. | |
| 4,895,841 A | 1/1990 | Sugimoto et al. | |
| 4,966,768 A | 10/1990 | Michelucci et al. | |
| 6,177,430 B1 | 1/2001 | Thompson et al. | |
| 6,287,599 B1 | 9/2001 | Burnside et al. | |
| 6,335,467 B1 | 1/2002 | Englert et al. | |
| 6,368,628 B1 | 4/2002 | Seth | |
| 6,528,685 B2 | 3/2003 | Cohen et al. | |
| 6,835,853 B2 | 12/2004 | Hoorn et al. | |
| 6,965,051 B2 | 11/2005 | Hoorn et al. | |
| 7,018,658 B2 | 3/2006 | Platteeuw | |
| 2003/0147955 A1* | 8/2003 | Platteeuw et al. | 424/469 |
| 2004/0096502 A1 | 5/2004 | Platteeuw | |
| 2005/0100602 A1* | 5/2005 | Sako et al. | 424/468 |
| 2005/0100603 A1* | 5/2005 | Sako et al. | 424/468 |
| 2008/0075775 A1* | 3/2008 | Gan et al. | 424/473 |

FOREIGN PATENT DOCUMENTS

| | | |
|---|---|---|
| EP | 0 034 432 B1 | 8/1981 |
| EP | 0 257 787 B1 | 3/1988 |
| EP | 0 186 087 B1 | 8/1989 |
| EP | 0 194 838 B1 | 9/1993 |
| EP | 0 533 297 | 11/1997 |
| EP | 0 309 157 A1 | 5/2000 |
| WO | WO 94/06414 | 3/1994 |
| WO | WO 00/27364 | 5/2000 |
| WO | WO 2004/078212 | 9/2004 |

OTHER PUBLICATIONS

NDA 20-579, FDA Office of Clinical Pharmacology and Biopharmaceutics Review, pp. 1-6, 1997.
Flowmax, MIMMS Abbreviated Prescribing Information, MIMMS Australia, 1996-2002.
Presentation entitled: "In Vivo Performance of Hydrophilic Matrix Tablets Utilizing HPMC: Case Studies" by Tim D. Cabelka, Ph.D. and Thomas D. Reynolds, Ph.D., The Dow Chemical Company, Oct. 17, 2000.
FDA—FOIA Labeling Information for Flomax®, 2001.
Dunn CJ, Matheson a and Faulds DM. "Tamsulosin A review of its pharmacology and therapeutic efficacy in the management of lower urinary tract symptoms." *Drugs Aging* 2002; 19; 135-161.
Dutkiewics S. "Efficacy and tolerability of drugs for treatment of benign prostatic hyperphasia." *Int Urology and Nephrology* 2001; 32; 423-432.
Harada K. and Fujimara A. "Clinical pharmacology of 1-A selective and nonselective 1-blockers." *BJU International* 2000; 86; 31-35.
Lyseng-Williamson KA, Jarvis B and Wagstaff AJ "Tamsulosin an update of its role in the management of lower urinary tract symptoms." *Drugs* 2002; 62; 135-167.
Michel MC, Neumann HG, Mehlburger L, Schumacher H and Goepel M. "Does the time for administration (morning or evening) affect the tolerability or efficacy of tamsulosin? *BJU International* 2001; 87; 31-34.
Soeishi Y, Korobi M, Kobayashi SI and Higuchi S. "Sensitive method for the determination of tamsulosin in human plasma using high-performance liquid chromotography with fluorescence detection" *J of Chromotography* 1990; 553; 291-296.
Taguchi K. Schafers RF and Michel MC. "Radioreceptor assay analysis of tamsulosin and terazosin pharmacokinetics." *Br J Clin Pharmacol.* 1998; 45; 49-55.
Van Hoogdalem EJ, Soeishi Y, Matsushima H and Higuchi S. "Disposition of the selective adrenoceptor antagonist tamsulosin in humans: Comparison with data from interspecies scaling." *J Pharm Sciences* 1997; 86; 1156-1161.

(Continued)

*Primary Examiner* — James H Alstrum Acevedo
(74) *Attorney, Agent, or Firm* — Muncy, Geissler, Olds & Lowe, PLLC (57) ABSTRACT

A tamsulosin controlled release tablet is formed using a water-swellable matrix-forming composition as a release controlling mechanism. The matrix forming composition comprises (i) a pH-sensitive swellable hydrophilic polymer, which is a cross-linked polyacrylic acid polymer, and (ii) a pH-insensitive swellable hydrophilic polymer. The tablet optionally contains a water insoluble binder as well.

20 Claims, 4 Drawing Sheets

OTHER PUBLICATIONS

Rabasseda and Fitzpatrick, "Tamsulosin: The First Prostate-Selective alpha 1a-Adrenoceptor Antagonist for Treatment of Symptomatic Benign Prostatic Hyperplasia," Drugs of Today, vol. 32, No. 3, 1996, pp. 259-268.

* cited by examiner

TABLET COMPOSITION WITH A PROLONGED RELEASE OF TAMSULOSIN

This application claims the benefit of priority from prior U.S. provisional patent application No. 60/801,135, filed May 17, 2006, and from U.S. provisional patent application No. 60/914,148, filed Apr. 26, 2007, the entire contents of each provisional application being incorporated herein by reference.

BACKGROUND OF THE INVENTION

Tamsulosin is a known chemical compound having alpha-adrenergic blocking activity that is useful for treatment of cardiac insufficiencies and benign prostatic hyperplasia (BPH). Tamsulosin is the common name for (R)-5-[2-[[2-(2-ethoxyphenoxy)ethyl]amino]propyl]-2-methoxy-benzene-sulfonamide. It is disclosed in EP 34432 and U.S. Pat. No. 4,731,478.

Several medicaments comprising tamsulosin, specifically tamsulosin hydrochloride, are currently marketed. The first commercially available medicament comprising tamsulosin (OMNIC, FLOMAX, marketed since 1993) were gelatin capsules filled with pellets comprising tamsulosin. In Japan, an orally-disintegrating tablet based on a WOWTAB technology (Harnal D), is also on the market.

Recently a tablet formulation was introduced on the market in Europe (Omnic OCAS, Mapelor OCAS), having a prolonged release of the active component. The tablet is purported to have less or no food effect in comparison to the capsule formulations. This marketed tablet medicament uses the so called OCAS drug delivery system which enables gradual release of a drug as the tablet travels through the digestive tract, including the colon. It appears that the relevant patent covering the OCAS delivery system is a patent family based on WO 94/06414 (EP 661045, U.S. Pat. No. 6,436,441).

In general, the OCAS system comprises a drug, a hydrogel-forming polymer and a highly water soluble hydrophilic additive (a "hydrophilic base"), which is important in aiding rapid water penetration into the core. The concept is that the preparation absorbs water as it enters and passes through the upper digestive tract such that the water-swellable polymer undergoes substantially complete gelation (i.e. at least 70%). As the preparation continues down the digestive tract, its gelled surface continues to constantly erode, thereby maintaining a release of the drug even in the lower digestive tract, e.g., in the colon.

The stability and the rate of formation of the gel layer, as well as the rate of its erosion after prolonged hydration are important factors in designing an OCAS tablet. Too little hydrophilic base can lead to insufficient gelation such that release in the colon is compromised. Too much hydrophilic base can result in a gel that is too fragile and/or release of the drug that is too rapid. In addition to these gelation/viscosity issues, the hydrogel-forming polymer should also preferably be selected so as to provide sufficient mechanical strength so that the tablet can essentially retain its shape during its travel in spite of the contractile forces of the digestive tract.

In view of the above, the hydrogel-forming polymer which can be used in the OCAS system as the matrix-forming agent is preferably a polymer showing a high viscosity on gelation, e.g., a viscosity of not less than 1000 cps in 1% aqueous solution (at 25° C.). Because viscosity of the gel depends in part on the molecular weight, the hydrogel-forming polymer is preferably a substance having a high molecular weight of not less than 2 million and more preferably of not less than 4 million. A preferred hydrogel-forming polymer according to U.S. Pat. No. 6,436,441 is a poly(ethylene oxide), especially one having a molecular weight of not less than 2 million.

The actually marketed OCAS tablet comprising tamsulosin (or "TOCAS" tablet) comprises a high molecular weight poly(ethylene oxide) as the hydrogel-forming polymer and a polyethylene glycol as the solubility enhancing hydrophilic base. The TOCAS tablets are film coated, which coating contains hydroxypropylmethyl cellulose.

WO 2004/078212 teaches that manufacturing a tablet based on poly(ethylene oxide) with a molecular weight of 2,000,000 or higher as taught in U.S. Pat. No. 6,436,441, is difficult. For instance, the polymer becomes very sticky when exposed to moisture. Additionally, granulating the polymer turned out to be problematic. And because the intended/preferred drug, tamsulosin hydrochloride, is used in low doses, the patent publication teaches that direct compression and dry granulation are unsuited because of content uniformity concerns; e.g., the drug concentration may not be uniform throughout the tabletting blend which leads to variable dosage strengths. To address these manufacturing issues, WO 2004/078212 proposes "sizing" particles of poly(ethylene oxide) by spraying an aqueous solution or suspension of a sizing agent onto the particles and drying the particles. The sizing agent is typically a portion of the polyethylene glycol used as the hydrophilic base. Generally the drug, which is preferably tamsulosin HCl, is included in the aqueous solution/suspension of the sizing agent. The resulting poly(ethylene oxide)-containing granulate is purported to be readily incorporated into a finished dosage form such as a tablet by conventional techniques.

It would be desirable to find an alternative delivery system for providing tamsulosin release throughout the whole digestive tract. Furthermore, it would be advantageous to find a tablet delivery system for the continual tamsulosin release throughout the whole digestive tract that can be prepared by a simple direct compression of the drug and matrix components.

SUMMARY OF THE INVENTION

The present invention is based on the discovery of controlled release tamsulosin tablets that can be easily manufactured and that can provide long duration of release. Accordingly, a first aspect of the invention relates to a controlled release pharmaceutical tablet comprising:
a) 0.1 to 1 weight % of tamsulosin, preferably tamsulosin hydrochloride;
b) 40-80 weight % of a water-swellable matrix-forming composition comprising (i) a pH-sensitive swellable hydrophilic polymer, which is a cross-linked polyacrylic acid polymer, and (ii) a pH-insensitive swellable hydrophilic polymer; and
c) optionally a water insoluble binder.

Preferably the pH-sensitive polymer is a carbomer and the pH-insensitive polymer preferably is a linear polymer such as hydroxypropyl methylcellulose (HPMC), especially a high molecular weight HPMC. The relative amount of the pH-sensitive polymer in the matrix-forming composition is generally a minority portion, though it can be up to about 60%, and is typically within the range of 5%-50% of the matrix-forming composition. The produced tablet preferably comprises from 0.1 to 1 mg of tamsulosin, calculated as the hydrochloride, and generally has a mass from 50 to 300 mg.

The selection of the two kinds of swellable polymers with different properties and in various amounts allows the release rate of the tamsulosin from the tablet to be controlled. Generally, the in vitro dissolution shows that the tablet is still releasing tamsulosin even after 18 hours. The selection of the pH-sensitive and pH-insensitive polymers can advantageously be directed to the kinds and brands which are compressible into a tablet without having to incorporate them into granules via wet granulation. In this regard the optional binder can facilitate efficient tabletting.

Another aspect of the invention relates to a process for making a tamsulosin tablet, which comprises:
(a) wet granulating at least a water-insoluble binder and tamsulosin or a salt thereof to form a granulate;
(b) blending said granulate in one or more steps with at least a pH-sensitive swellable hydrophilic polymer, which is a cross-linked polyacrylic acid polymer, and a pH-insensitive swellable hydrophilic polymer, to form a tablet blend containing 0.1 to 1% of said tamsulosin or salt thereof, 40% to 80% of said pH-sensitive and pH-insensitive swellable hydrophilic polymers, and up to 55% of said binder; and
(c) compressing at least a portion of said tablet blend to form a tablet.

The process is especially useful in making larger tablets having very low tamsulosin drug concentrations.

DETAILED DESCRIPTION OF THE INVENTION

The present invention provides a controlled release tablet for delivering tamsulosin for a long duration. Preferably the tablet delivers tamsulosin throughout the entire digestive tract, including the colon and/or does not reach 100% release of the tamsulosin until after 18 hours in a dissolution test, as described in more detail hereinafter.

The tamsulosin drug contained in the tablet can be tamsulosin or a salt thereof, and is generally tamsulosin hydrochloride. The amount of the tamsulosin drug in the composition is from 0.1 to 1 wt % (typically about 0.1 to 0.5%), expressed as tamsulosin hydrochloride. In absolute terms, each tablet contains from 0.1 to 1 mg, preferably 0.2, 0.4 or 0.8 mg, of tamsulosin, expressed as tamsulosin hydrochloride.

The tablet comprises a water-swellable matrix-forming composition, which serves as the primary control of the release of the tamsulosin drug, in an amount typically within the range of 40% to 80%, preferably 50-70%, of the tablet mass (note that all percentages used herein refer to weight percent unless otherwise indicated). The composition comprises two types of matrix-forming polymers, which are described below.

The first matrix-forming component of the matrix-forming composition is a pH-sensitive swellable hydrophilic polymer, i.e. a polymer that swells in water and produces hydrogels in a rate and amount that is dependent on the environmental pH-range. The pH-sensitive swellable hydrophilic polymer used in the present invention is a cross-linked polyacrylic acid polymer. The most preferred such polymer in the compositions of the present invention is a carbomer. Carbomers are synthetic high-molecular-weight polymers of acrylic acid that are crosslinked with either allyl sucrose or with allyl ethers of pentaerythritol. They contain from 56 to 68% of carboxylic acid groups, when calculated on a dry basis. Their molecular mass cannot be directly evaluated due to the presence of the crosslinker, but is estimated from 700,000 to 4 billion. Carbomers disperse (do not dissolve) in water to form acidic colloidal solutions of low viscosity, however, when neutralized at above the pK value (approximately at pH>5.5), they produce highly viscous gels.

Within a tablet and in an aqueous environment, the carbomer produces a hydrogel mass, often referred to as a hydrogel layer. Due to the crosslinking, the gel does not erode in the gastrointestinal tract (as is common in the case of gels formed from hydrophilic linear polymers) and releases the drug mainly by a diffusion mechanism.

The pharmaceutically acceptable types of carbomer polymers differ from each other by the type of cross linker, percentage of the crosslinker, and residual solvents used for polymerization. While the Ph. Eur. has a single monograph for the whole class of carbomers, the USP has several monographs. The most preferred types of carbomers in compositions of the invention are those having an extra low content of residual polymerization solvent, because of the intended use in oral preparations. In general, such suitable carbomers are marketed with a letter P after its name. Furthermore, it is preferred that the dynamic viscosity of the carbomer polymer measured in aqueous solution is sufficiently high (preferably at least 4000 mPa/s, measured at 0.5% aqueous solution); however the dynamic viscosity of carbomers in plain water is not a limiting factor in the compositions of the present invention.

Taking the above in consideration, various marketed carbomers, e.g., under the brand name Carbopol® (Noveon, Inc., Cleveland, Ohio, USA), are suitable for making the tablets of the present invention. These include Carbopol 934P, which is crosslinked with an allyl sucrose and is polymerized in benzene; and Carbopol 71G, Carbopol 974P and Carbopol 971P, which are crosslinked with an allyl pentaerythritol and polymerized in ethyl acetate. Carbopol 71G is a granulated form of Carbopol 971P.

Carbomers, in general, have good tabletting properties and good binding properties; therefore they are suitable for a variety of tabletting processes including those that do not use a liquid. The Carbopol 71G is particularly useful in certain embodiments of the invention as it is a granulated product with good handling properties and readily tablettable by a direct compression process.

The relative mass amount of the pH-sensitive swellable polymer, and specifically the carbomer, in the compositions of the present invention may vary from 4 or 5% to 60% of the mass of the matrix-forming composition. In some embodiments, such as larger tablets having a weight greater than 200 mg, the relative amount of the pH-sensitive swellable polymer in the matrix-forming composition is frequently low such as in the 5-25% range. In other embodiments such as in smaller tablets having a weight of 100 mg or less, the relative amount of the pH-sensitive swellable polymer in the matrix-forming composition is generally a little higher such as 10% to 60%, typically 10 or 15% up to 40 or 50%. Alternatively or additionally, the amount of the pH-sensitive swellable polymer relative to the overall tablet mass is generally in the range of 3% to 30% and typically in the range of 5% to 30% of the overall mass of the tablet.

The second matrix-forming component is a pH-insensitive swellable hydrophilic polymer, which is preferably a linear (i.e. not crosslinked) polymer. The pH-insensitive hydrophilic polymer can preferably produce a viscous gel and is at least swellable independently of the pH of the environmental fluid. If the polymer is linear, the gel of such polymer is water soluble and it releases the drug by a mechanism, which is different from that of the crosslinked polymer, mostly by slow erosion and continual dissolution of the gel in the body fluid.

A preferred compound among the pH-insensitive swellable hydrophilic polymers is a hydroxypropyl methylcellulose (HPMC), particularly a high viscosity grade HPMC. The dynamic viscosity of HPMC can affect the overall release rate. In compositions of the invention, the HPMC brand should typically have a nominal dynamic viscosity of at least about 100,000 mPa/s (which actually means the actual viscosity range from about 80,000 to 120,000 mPa/s), when measured in a 2% (w/v) aqueous solution at 20° C. A preferred HPMC brand is Methocel K100 MCR (Dow Chemicals, USA).

Apart from the high viscosity HPMC, also high viscosity pH-insensitive linear polyacrylates and polymethacrylates may be used, and accordingly any high molecular weight pH-insensitive polymer, and preferably a linear polymer, that may quickly form a viscous gel (e.g., hydroxypropylcellulose, hydroxyethylcellulose, etc,) can be used. Additional pH-insensitive swellable hydrophilic polymers (e.g. kollidon SR, polymethacrylates, etc) which are generally not gel forming but are merely swellable can also be used, but are somewhat less preferred than a gel forming polymer such as HPMC. Also a combination of two or more types and/or kinds of pH-insensitive polymers may be used to form the pH-insensitive swellable hydrophilic polymeric component of the water-swellable matrix-forming composition.

In respect to the tabletting process, care is generally taken that the pH-insensitive polymer should also have good tabletting properties (flowability, physical stability, etc.). It should preferably not be thermoplastic and be non-hygroscopic. Thus, for instance, poly(ethylene oxide) is not preferred, and is desirably avoided, for use in the composition of the present invention as it suffers from bad tabletting properties, particularly in a repeated industrial tabletting process.

The relative amount of the pH-insensitive swellable polymer, and specifically the HPMC, in the compositions of the present invention plays a role in the overall release rate and should be more than 30%, generally from 40-95% and typically from 50 or 60% to 85 or 90% of the mass of the matrix-forming composition. In correspondence to the pH-sensitive swellable polymer component of the matrix-forming composition, the range of the relative amount of the pH-insensitive swellable polymer is somewhat a function of overall tablet weight. Accordingly, a larger tablet generally uses the higher ranges of the pH-insensitive swellable polymer such as 70-95% while the smaller size tablets generally use slightly lower relative amounts of the pH-insensitive swellable polymer such as 50-90%. Alternatively or additionally, the amount of the pH-insensitive swellable polymer relative to overall tablet mass is generally from 20 to 70% of the overall mass of the tablet composition.

While not required, the presence of a binder in the tablet composition is generally advantageous. Water insoluble binders are well known in the art. A suitable binder is microcrystalline cellulose as it also aids in achieving good content uniformity of the tablets (tablet blends), even in the case of such a small amount of the active substance as in the present tamsulosin tablets. Other suitable binders include methyl cellulose and/or starch. The amount of the binder generally does not exceed 55% and typically is about 10-55%, more typically 15 to 50%, of the total mass of the tablet composition.

Furthermore, the tablet may contain other excipients. In particular, these excipients are added to improve the flowing properties (e.g., glidants such as talc, colloidal silicone dioxide, etc.) and/or to minimize the stickiness to tablet punches (lubricants such as magnesium stearate, calcium stearate, glyceryl behenate, etc.). Non-functional excipients such as microbial preservatives, colorants, flavorants, etc., can also be used in the composition. In general, their amounts are very low and do not affect the release rate. It should be noted that solubility-enhancing agents, i.e. highly water soluble compounds such as mannitol, lactose, polyethyleneglycol, etc., are not necessary in the compositions of the present invention and preferably are avoided from the tablet composition. Their presence would generally negatively affect the release rate during the first two hours of release.

Enteric coating of the tablets is, in essence, not necessary. However, if desired, a tablet may be film-coated to improve its appearance and/or handling, using conventional film-coating materials and techniques. Such a film-coat does not substantially affect the release rate. Also, the weight of such a cosmetic coating, if present, is not included in the overall or total mass of the tablet for purposes of calculating the above-mentioned component percentages.

The overall mass of the tablet is generally from 50 to 300 mg. In some embodiments the tablet 50 to 200 mg, advantageously from 75 to 100 mg. In other embodiments, the tablet is slightly larger such as 150-300 mg, advantageously 200-260 mg. The tablets preferably exhibit the hardness from about 40 to about 130 N. The amount of the tamsulosin drug (calculated as tamsulosin hydrochloride) in a tablet is preferably from 0.1 to 1 mg.

By selecting the water-swellable matrix-forming polymeric components, including the polymer species and their relative amounts, as well as the overall amount of the matrix-forming composition in the tablet, the controlled release of tamsulosin can be manipulated to a desired release profile. To provide a tablet that releases tamsulosin for a long time and preferably even in the colon, the tablet should typically have an in vitro dissolution profile such that tamsulosin is still being released after 18 hours. That is, less than 100% of the tamsulosin is released at 18 hours, preferably no more than 97%, more preferably not more than 95% is released at 18 hours, using a two step dissolution media test. As used herein, a "two step dissolution media test" means an in vitro dissolution test wherein the tablets are first immersed for 2 hours in simulated gastric fluid (typically without enzymes as is common in the art), and afterwards in phosphate buffer of pH 6.8 to simulate intestinal fluid. The testing is performed in conventional Ph. Eur. or USP apparatus, by a paddle method. That a tablet has not finished releasing the tamsulosin at 18 hours, but rather is still releasing tamsulosin, is a good indication that in vivo the tamsulosin will be released throughout the digestive tract, including the colon.

In general, the tablets of the invention typically meet the following dissolution criteria when subjected to a dissolution test under appropriate conditions: less than 40% of tamsulosin is released within 2 hours; less than 60% is released in 6 hours; and less than 80% is released in 10 hours. Preferably the dissolution curve or profile is such that less than 80% is released in 12 hours. Appropriate conditions for a dissolution test are routinely determined by workers of ordinary skill in the art for a given tablet. A dissolution test described in a new (or abbreviated new) drug application for a tamsulosin tablet that a regulatory authority such as the U.S. FDA finds acceptable is an example of a dissolution test performed under "appropriate" conditions (hereinafter an "FDA-approved test"). Using an FDA-approved test is a preferred "appropriate" set of conditions for determining the dissolution profile and for determining whether the above-described profile is met. The above-described two-step dissolution test can also be used. Typically the dissolution media in an appropriate dissolution test is a phosphate buffer or other simulated intestinal fluid at pH 6.8. The testing is performed in conventional Ph. Eur. or USP apparatus, by a paddle or a basket method using conventional rotation speeds. In one embodiment the testing is performed in a single dissolution medium of simulated intestinal fluid (pH 6.8) by a paddle method, preferably at 50 rpm. The use of so-called Japanese basket is advantageous as greater uniformity of results may be obtained.

In a preferred embodiment, the tablets of the present invention do not exhibit a food effect. That is, the tablets can be administered to a patient in either a fasted or a fed state without significantly affecting the release/bioavailability of the tamsulosin.

The tablets of the present invention can be made by any known tabletting technique including wet granulation, direct compression, etc. Two processes are particularly favored: direct compression and a partial wet granulation technique.

Processes in which a liquid is absent; i.e., the tablets are formed by a dry process, are commercially attractive due to ease of manufacture. A dry process includes direct compression and dry granulation but excludes techniques that require a liquid such as water and/or its subsequent removal; e.g. wet granulation or the aqueous spray "sizing" of the above-described prior art. Although dry processes for making tablets are well known, typically such processes are not recommended for tablets having a low content of active substance for fear that insufficient content uniformity would result. Surprisingly, controlled release tablets of the present invention can be made by dry processes, even though the amount of tamsulosin drug contained therein is low (less than 1%) and yet still obtain consistent content uniformity. Apparently one or more of the free flowing excipients in the tablet composition may serve as a suitable solid diluent in which the tamsulosin may be homogeneously dispersed, e.g. by mixing and milling of the tamsulosin/excipient mixture. Such a homogeneous dispersion is then mixed with the rest of the excipients and homogenized again. The polymers in the matrix-forming composition can be selected in such a way that their physical properties are not substantially altered during the blending process (in particular, they do not absorb moisture in such an extent that the flowability of the powder is affected and do not become plastic during mixing and/or milling) and they are directly tablettable.

The tablet blend is compressed into a tablet by a direct compression process, i.e. a portion of the tablet blend, including a lubricant and glidant, is dosed onto a tablet punch of a proper shape and compressed to form a tablet. However, a conventional dry granulation process followed by the compression of the granulate may be used as well.

The dry process tabletting techniques are especially advantageous for making smaller tablets of the invention. Tablets of approximately 50-150 mg, especially 75-100 mg, can be made in a repeatable, robust direct compression tabletting technique with acceptable content uniformity. Another process, which Can be used for any size tablet and is especially useful for making larger tablets, such as 200-300 mg, uses wet granulation to form a granulate of the tamsulosin active before mixing the tablet blend.

In more detail, the tamsulosin or its salt and a binder are wet granulated to form a granulate. The granulate can contain additional excipients and typically contains a small amount (e.g. 1-10%) of the pH-insensitive swellable hydrophilic polymer discussed above. Usually the granulate does not contain any further ingredients or excipients, but such is not excluded. A typical granulate would thus contain at least 80%, more typically at least 90% of water-insoluble binder, which may or may not represent all of the binder contained in the tablet. A suitable liquid medium for wet granulation is water, which is substantially removed from the granulate and/or from the subsequent tablet blend by conventional drying before tabletting/compression. The granulate (which typically represents 20-40% of the total mass of the tablet) is then dry mixed with at least the pH-insensitive swellable hydrophilic polymer, or the remainder thereof, and the pH-sensitive swellable hydrophilic polymer discussed above, in one or more steps to form a tablet blend. Additional excipients such as a lubricant, etc., are typically also included in the tablet blend and are added together with, or separately from, the matrix-forming polymers in the same or different mixing steps. Generally no additional active is added; i.e. no extra-granular tamsulosin or salt thereof. Binder, however, can be further added, i.e. both intra-granular and extra-granular binder can be present in the tablet. Typically most or all of the binder is intra-granular, e.g. at least 60% and generally 70% to 95% when some is contained extra-granular. The resulting tablet blend is then compressed into tablets by conventional techniques. The matrix-forming polymers are generally contained extra-granular but can also be present to some extent intra-granular. The partial wet granulation technique can improve content uniformity between tablets which can be a concern as the relative amount of tamsulosin drug becomes very small; e.g., low doses of tamsulosin in larger tablets.

The tablets may be used in treatment of tamsulosin-treatable diseases, especially BPH, in dosages and regimens similar to the marketed tamsulosin-OCAS tablets. The invention is further illustrated by the following non-limiting examples.

Example 1

Direct Compression

Four batches of tablets were prepared having the following compositions (in weight %):

|  | Batch 1 | Batch 2 | Batch 3 | Batch 4 |
|---|---|---|---|---|
| Tamsulosin HCl | 0.5 | 0.5 | 0.5 | 0.5 |
| HPMC K100MCR | 40 | 50 | 50 | 60 |
| Carbomer 71 G NF | 20 | 10 | 15 | 10 |
| MCC | 38.5 | 38.5 | 33.5 | 28.5 |
| Silicon dioxide | 0.5 | 0.5 | 0.5 | 0.5 |
| Mg stearate | 0.5 | 0.5 | 0.5 | 0.5 |

Manufacturing Process

The silicon dioxide was sieved over a 0.6 mm sieve. Tamsulosin hydrochloride was mixed with a part of HPMC in weight ratio 1:10 in a Turbula mixer for 15 minutes at 46 rpm, the mixture was then milled for 30 seconds in a coffee mill and mixed for another 5 minutes in the Turbula at 46 rpm. The remaining HPMC, microcrystalline cellulose (MCC), carbomer and silicon dioxide were added and mixed for another 15 minutes at 46 rpm. Magnesium stearate was sieved over a 0.8 mm sieve and added to the blend. The whole blend was mixed for another 5 minutes at 22 rpm.

The blend was compressed into round tablets of a diameter of 6 mm and 80 mg weight, with a hardness of 50 N. Dissolution profiles were measured with 2 hours in SGF (pH 1.2 and without enzymes) followed by 18 hours in a phosphate buffer of pH 6.8. Dissolution profile (USP apparatus II) was measured using three tablets each in 500 ml of the corresponding buffer at a rotation speed of 100 rpm and a temperature of 37° C. The resulting average release profiles for each of Batches 1-4 are shown in FIGS. 1-4, respectively, wherein "TSL" refers to tamsulosin.

Example 2

Tablets Made by Partial Wet Granulation

A batch of tablets was prepared having the following composition:

| | % (based on total tablet wt) | mg |
|---|---|---|
| Granulate | | |
| Tamsulosin HCl | 0.17 | 0.4 |
| HPMC K100MCR | 1.42 | 3.401 |
| MCC PH 101 | 28.84 | 69.209 |
| water | — | — |
| Total | — | 73.01 |
| Batch 5 | | |
| Granulate | 30.42 | 73.01 |
| MCC PH 102 | 5 | 12 |
| HPMC K100MCR | 58.58 | 140.59 |
| Carbomer 71GNF | 5 | 12 |
| Silica dioxide | 0.5 | 1.2 |
| Magnesium stearate | 0.5 | 1.2 |
| Tablet mass (mg) | — | 240 |
| Tablet diameter (mm) | — | 9 |

Manufacturing Process

The formulation given was made with the following processes: Tamsolusin hydrochloride, microcrystalline cellulose (MCC PH 101) and a part (1.42%) of the total hydroxypropyl methylcellulose were mixed in the VMA. The blend was mixed and water was added to the mixed blend until a granute was formed. The granulate was dried in the VMA with microwaves, vacuum and a bowl temperature of 60° C. The granulate was milled through a 0.5 mm sieve. Silica dioxide was mixed with a part of the microcrystalline cellulose and sieved over a 0.8 mm sieve. The magnesium stearate was sieved over an 800 µm sieve. The silica dioxide pre-mix and the half of the hydroxypropyl methylcellulose was added to the granulate and mixed for 15 minutes at 25 rpm in a Bohle free fall mixer. The remaining hydroxypropyl methylcellulose was added and the blend was mixed for another 15 minutes. Carbomer was added and the blend was mixed for 15 minutes. Magnesium stearate was added and the granulate was mixed for 5 minutes. The blend was compressed with a rotary press into 240 mg tablets with a diameter of 9 mm and a hardness of 80N.

Figure 1:
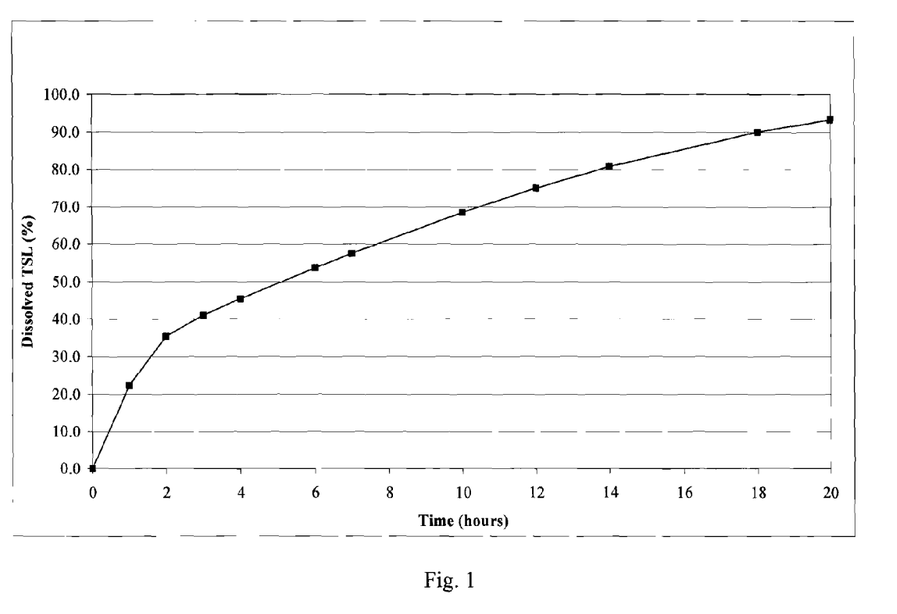
FIG. 1 shows the average release profile of the tablets made according to Batch 1 of Example 1 herein, using a two-step dissolution media test.
Figure 2:
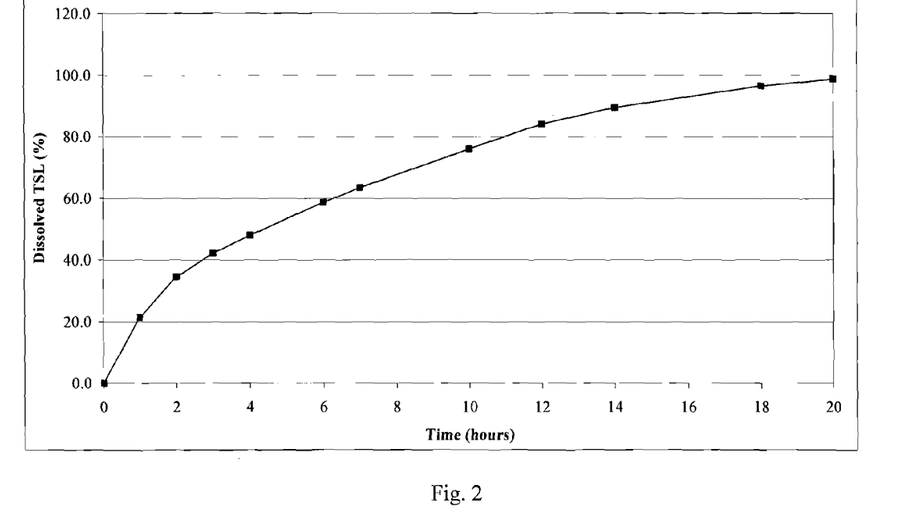
FIG. 2 shows the average release profile of the tablets made according to Batch 2 of Example 1 herein, using a two-step dissolution media test.
Figure 3:
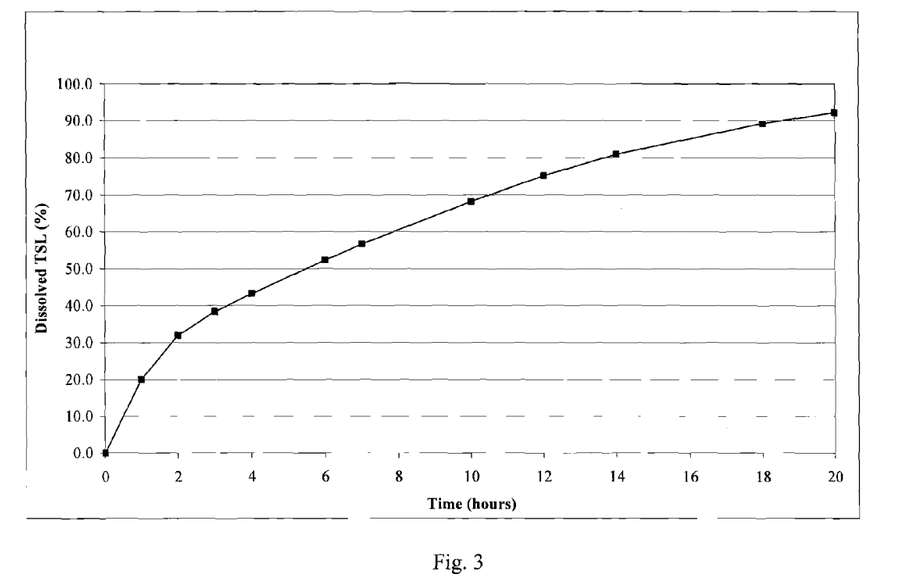
FIG. 3 shows the average release profile of the tablets made according to Batch 3 of Example 1 herein, using a two-step dissolution media test.
Figure 4:
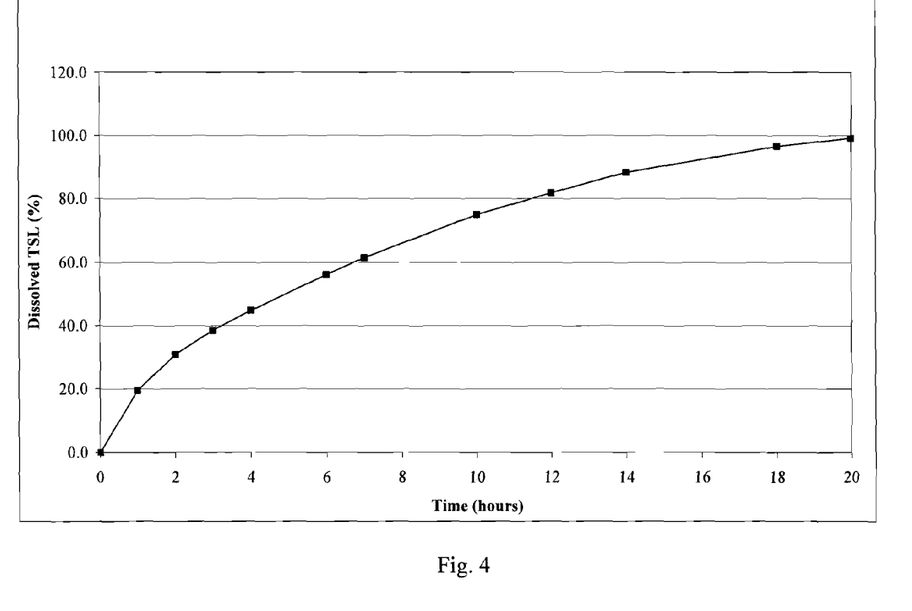
FIG. 4 shows the average release profile of the tablets made according to Batch 4 of Example 1 herein, using a two-step dissolution media test.
Figure 5:
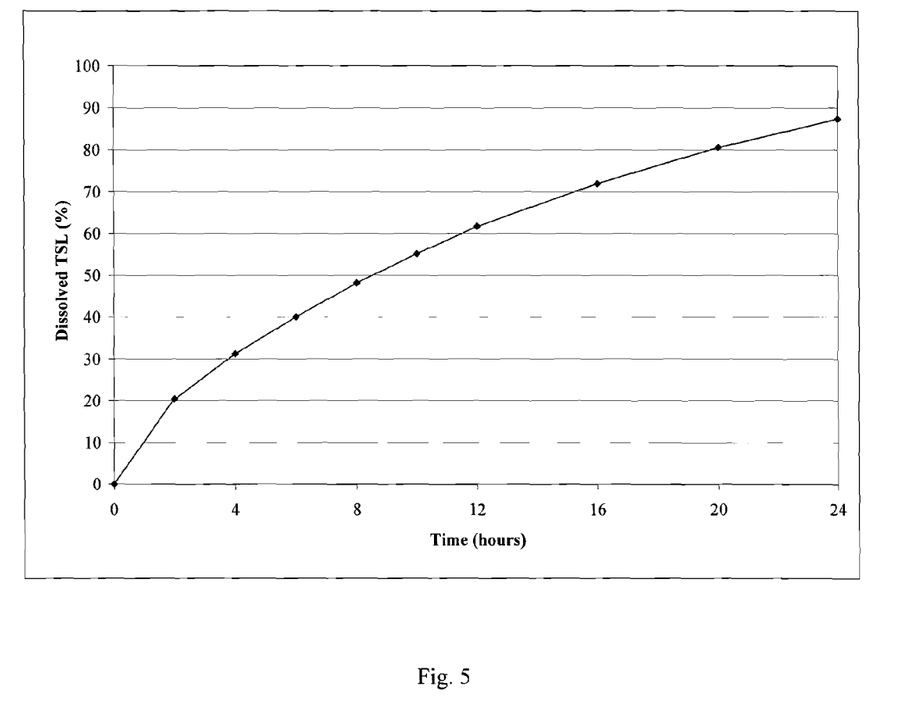
FIG. 5 shows the average release profile of the tablets made according to Batch 5 of Example 2 herein, using a single dissolution media test.

Testing conditions: Dissolution profile (USP apparatus II) was measured using six tablets each in 500 ml phosphate buffer pH 6.8 using a Japanese basket and a temperature of 37° C. Rotation speed is 50 rpm. The resulting averaged release profile is shown in FIG. 5, wherein "TSL" means tamsulosin.

Each of the patents, patent applications, and journal articles mentioned above are incorporated herein by reference. The invention having been described it will be obvious that the same may be varied in many ways and all such modifications are contemplated as being within the scope of the invention as defined by the following claims.

What is claimed is:

1. A controlled release pharmaceutical tablet comprising:
   a) 0.1 to 1 weight % of tamsulosin or a salt thereof;
   b) 40-80 weight % of a water-swellable matrix-forming composition comprising (i) a pH-sensitive swellable hydrophilic polymer, which is a cross-linked polyacrylic acid polymer, and (ii) a pH-insensitive swellable hydrophilic polymer; and
   c) optionally a water insoluble binder;
   wherein said tablet exhibits the following dissolution criteria when subjected to a dissolution test under appropriate conditions: less than 40% of tamsulosin is released in 2 hours, less than 60% of tamsulosin is released in 6 hours, and less than 80% of tamsulosin is released in 10 hours.

2. The tablet according to claim 1, wherein said pH-sensitive swellable hydrophilic polymer is a carbomer.

3. The tablet according to claim 2, wherein said pH-insensitive swellable polymer is HPMC.

4. The tablet according to claim 3, wherein said carbomer is a polyacrylic acid crosslinked with allyl sucrose or allyl ethers of pentaerythritol, having 56 to 68% of carboxylic acid groups, and having a molecular weight of about 700,00 to 4 billion.

5. The tablet according to claim 1, wherein 50%-70% of said tablet is said water-swellable matrix-forming composition.

6. The tablet according to claim 1, wherein 3% to 30% of said tablet is said pH-sensitive swellable hydrophilic polymer.

7. The tablet according to claim 1, wherein 20% to 70% of said tablet is said pH-insensitive swellable hydrophilic polymer.

8. The tablet according to claim 1, wherein at least 30% of said water swellable matrix is said pH-insensitive swellable hydrophilic polymer.

9. The tablet according to claim 1, wherein 5% to 60% of said water swellable matrix is said pH-sensitive swellable hydrophilic polymer.

10. The tablet according to claim 1, wherein said water-insoluble binder is present in an amount of 10-55%.

11. The tablet according to claim 10, wherein said binder is microcrystalline cellulose.

12. The tablet according to claim 1, wherein said tamsulosin or salt thereof is tamsulosin hydrochloride.

13. The tablet according to claim 12, which contains 0.2, 0.4, or 0.8 mg of tamsulosin HCl.

14. The tablet according to claim 1, wherein said dissolution test is a two-step dissolution media test comprising two hours in simulated gastric fluid and then subsequently in simulated intestinal fluid.

15. The tablet according to claim 1, wherein said dissolution test is conducted in phosphate buffer at pH 6.8.

16. The tablet according to claim 1, wherein said tamsulosin or salt thereof is 0.2, 0.4, or 0.8 mg of tamsulosin HCl; said pH-sensitive swellable hydrophilic polymer is a carbomer; said pH-insensitive swellable hydrophilic polymer is HPMC and is contained in an amount of 20% to 70% of said tablet and said binder is microcrystalline cellulose and is contained in an amount of 10% to 55% of said tablet.

17. A process for making tamsulosin tablet, which comprises:

(a) wet granulating at least a water-insoluble binder and tamsulosin or a salt thereof to form a granulate;
(b) blending said granulate in one or more steps with at least a pH-sensitive swellable hydrophilic polymer, which is a cross-linked polyacrylic acid polymer, and a pH-insensitive swellable hydrophilic polymer to form a tablet blend containing 0.1 to 1% of said tamsulosin or salt thereof, 40% to 80% of said pH-sensitive and pH-insensitive swellable hydrophilic polymers, and up to 55% of said binder; and
(c) compressing at least a portion of said tablet blend to form a tablet.

18. The process according to claim 17, wherein said granulate further contains a first portion of said pH-insensitive water swellable hydrophilic polymer and the remainder is added in said blending step (b).

19. The process according to claim 18, wherein said first portion of said pH-insensitive water swellable hydrophilic polymer is 1-10% of the total amount of said polymer contained in said tablet blend.

20. The process according to claim 17, wherein said tablet exhibits the following dissolution criteria when subjected to a dissolution test under appropriate conditions: less than 40% of tamsulosin is released in 2 hours, less than 60% of tamsulosin is released in 6 hours, and less than 80% of tamsulosin is released in 10 hours.

* * * * *